United States Patent
Saito et al.

(10) Patent No.: US 10,551,343 B2
(45) Date of Patent: Feb. 4, 2020

(54) METHOD OF INSPECTING GAS SENSOR AND METHOD OF MANUFACTURING GAS SENSOR

(71) Applicant: NGK INSULATORS, LTD., Nagoya-shi, Aichi (JP)

(72) Inventors: Naoya Saito, Slaskie (PL); Noriyuki Ina, Okazaki (JP); Kazuki Takegawa, Tokai (JP)

(73) Assignee: NGK INSULATORS, LTD., Nagoya (JP)

( * ) Notice: Subject to any disclaimer, the term of this patent is extended or adjusted under 35 U.S.C. 154(b) by 211 days.

(21) Appl. No.: 15/441,715

(22) Filed: Feb. 24, 2017

(65) Prior Publication Data
US 2017/0261466 A1   Sep. 14, 2017

(30) Foreign Application Priority Data
Mar. 9, 2016 (JP) .................................. 2016-045275

(51) Int. Cl.
*G01N 27/416* (2006.01)
*G01N 27/406* (2006.01)
*G01N 27/407* (2006.01)

(52) U.S. Cl.
CPC ..... *G01N 27/4163* (2013.01); *G01N 27/4067* (2013.01); *G01N 27/4073* (2013.01)

(58) Field of Classification Search
CPC ........ G01N 27/406–41; G01N 33/0004–0075; G01N 27/4163; G01N 27/4175;
(Continued)

(56) References Cited

U.S. PATENT DOCUMENTS 5,948,963 A  *  9/1999  Kato .................. G01N 27/4074
                                                        204/245
8,419,456 B2      4/2013  Masuda et al.
(Continued)

FOREIGN PATENT DOCUMENTS

EP       2333535 A1       6/2011
JP    2006-284223 A      10/2006
(Continued)

OTHER PUBLICATIONS

Nasu et al. (JP 2007225616 A, Machine Translation) (Year: 2007).*
(Continued)

*Primary Examiner* — Maris R Kessel
*Assistant Examiner* — Joshua L Allen
(74) *Attorney, Agent, or Firm* — Global IP Counselors, LLP

(57) ABSTRACT

Provided is a method of inspecting an assembly defect of a gas sensor in a mass-production process. The sensor element included in a second constituting member includes a heater therein and an electrode terminal for a heater in its surface, and the first constituting member includes a contact point member contacting the terminal in a state where the sensor element is inserted into its opening. A first heater resistance value before incorporated is measured to associate the resistance value with an identification information of the sensor element, a second heater resistance value is measured via a contact point member, in a state where the first and second constituting members are integrated with each other, to associate the resistance value with the identification information of the sensor element, and when a difference value between these resistance values associated with the identical identification information exceeds a threshold value, it is determined that an assembly defect occurs.

17 Claims, 11 Drawing Sheets

(58) Field of Classification Search
CPC .......... G01N 27/4073; G01N 27/4067; G01N 27/4078; G01N 27/4062
See application file for complete search history.

(56) References Cited

U.S. PATENT DOCUMENTS

| | | | |
|---|---|---|---|
| 2002/0060150 A1 | 5/2002 | Hashimoto et al. | |
| 2005/0022361 A1* | 2/2005 | Matsuo | G01N 27/4077 29/517 |
| 2005/0263396 A1* | 12/2005 | Naito | G01N 27/4071 204/424 |
| 2009/0126460 A1* | 5/2009 | Gardner | G01N 33/0031 73/31.06 |
| 2009/0242400 A1* | 10/2009 | Fujita | G01N 27/419 204/408 |
| 2010/0084287 A1* | 4/2010 | Teramoto | G01N 27/4067 205/785 |
| 2011/0252865 A1* | 10/2011 | Tokuda | G01N 15/0656 73/23.31 |
| 2012/0071042 A1* | 3/2012 | Masuda | G01N 27/4111 439/890 |
| 2012/0167656 A1* | 7/2012 | Verdier | F02D 41/1495 73/1.06 |
| 2014/0298931 A1* | 10/2014 | Oba | G01N 27/4062 73/866.5 |
| 2015/0276695 A1* | 10/2015 | Kaneblei | G01N 33/0006 73/1.06 |

FOREIGN PATENT DOCUMENTS

| | | | |
|---|---|---|---|
| JP | 2007-225616 A | | 9/2007 |
| JP | 2007225616 A | * | 9/2007 |
| JP | 4965356 B2 | * | 7/2012 |
| JP | 5082013 B2 | | 11/2012 |

OTHER PUBLICATIONS

Nagao et al. (JP 4965356 B2, Machine Translation) (Year: 2009).*
The Extended European Search Report for the corresponding European application No. 17158907.0 dated Jul. 17, 2017.

* cited by examiner

F I G. 4
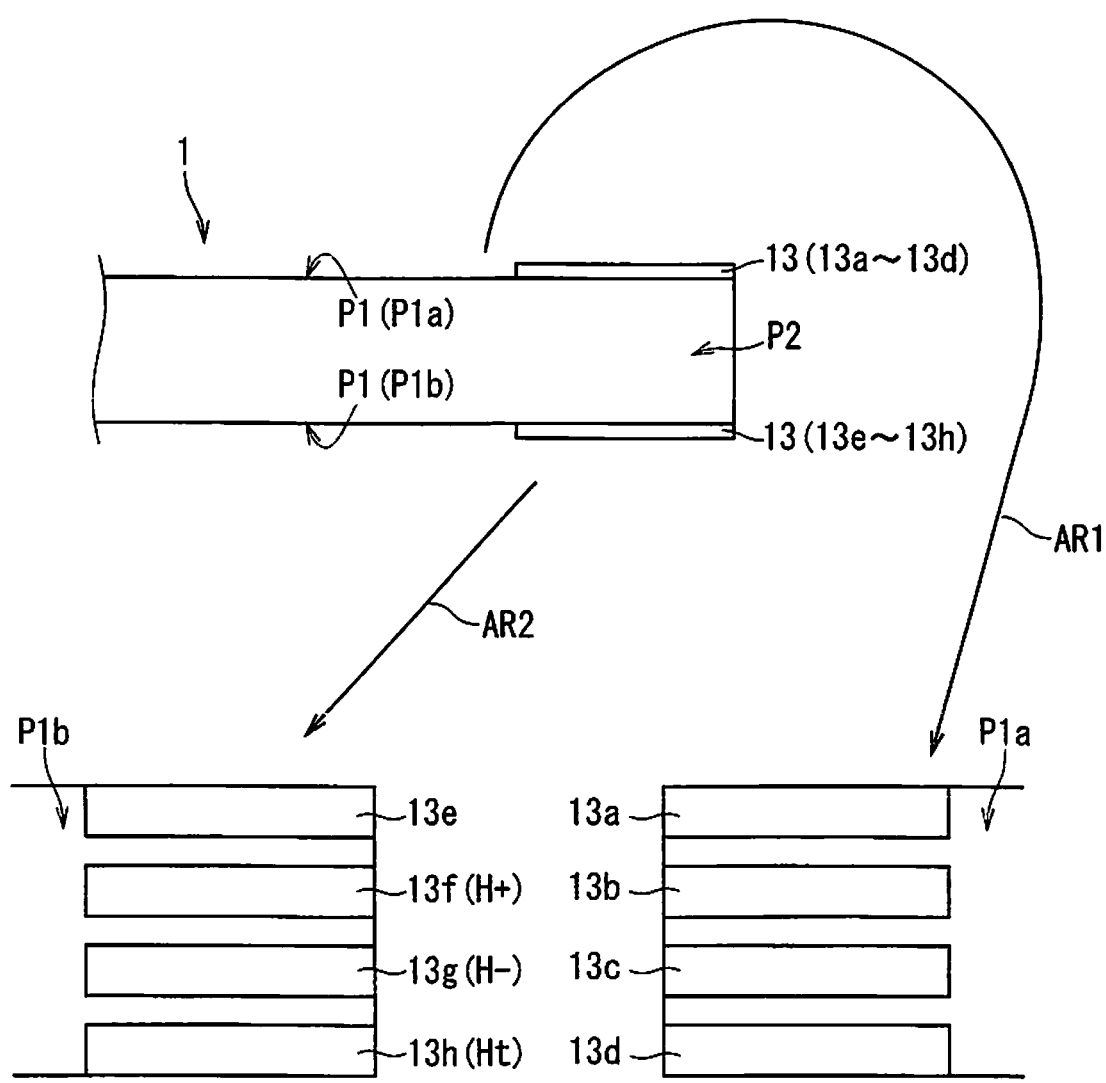

F I G. 7
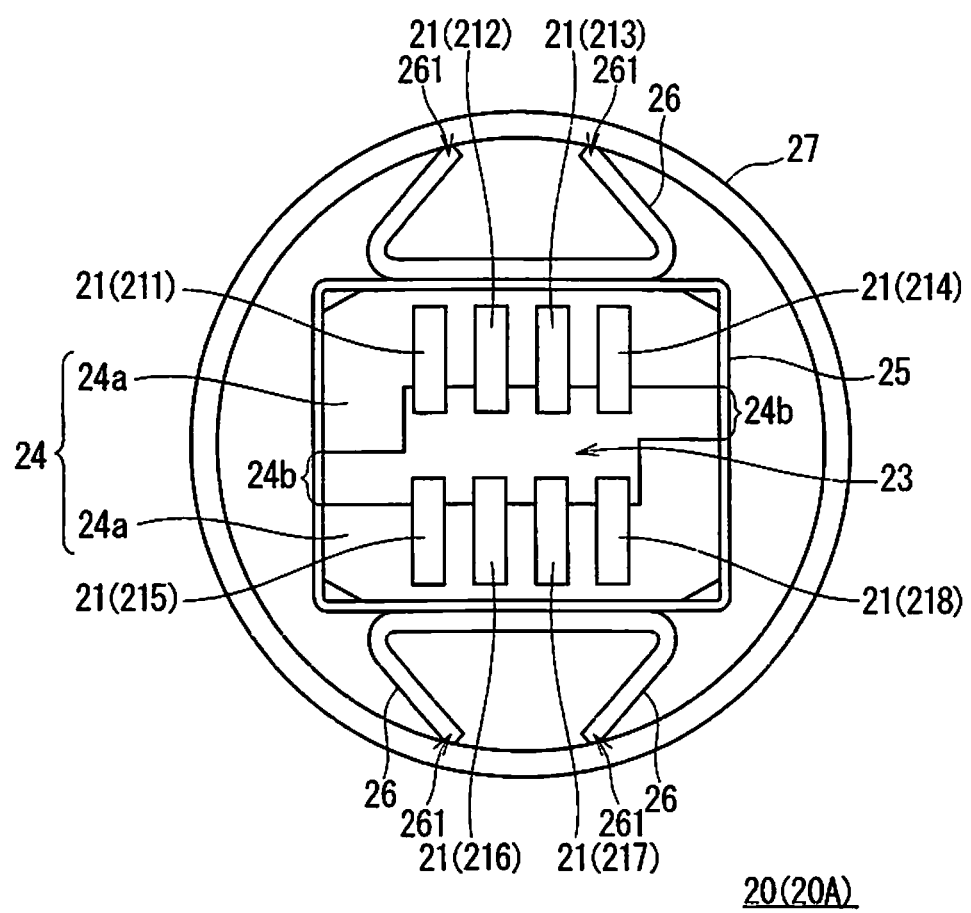

F I G. 9
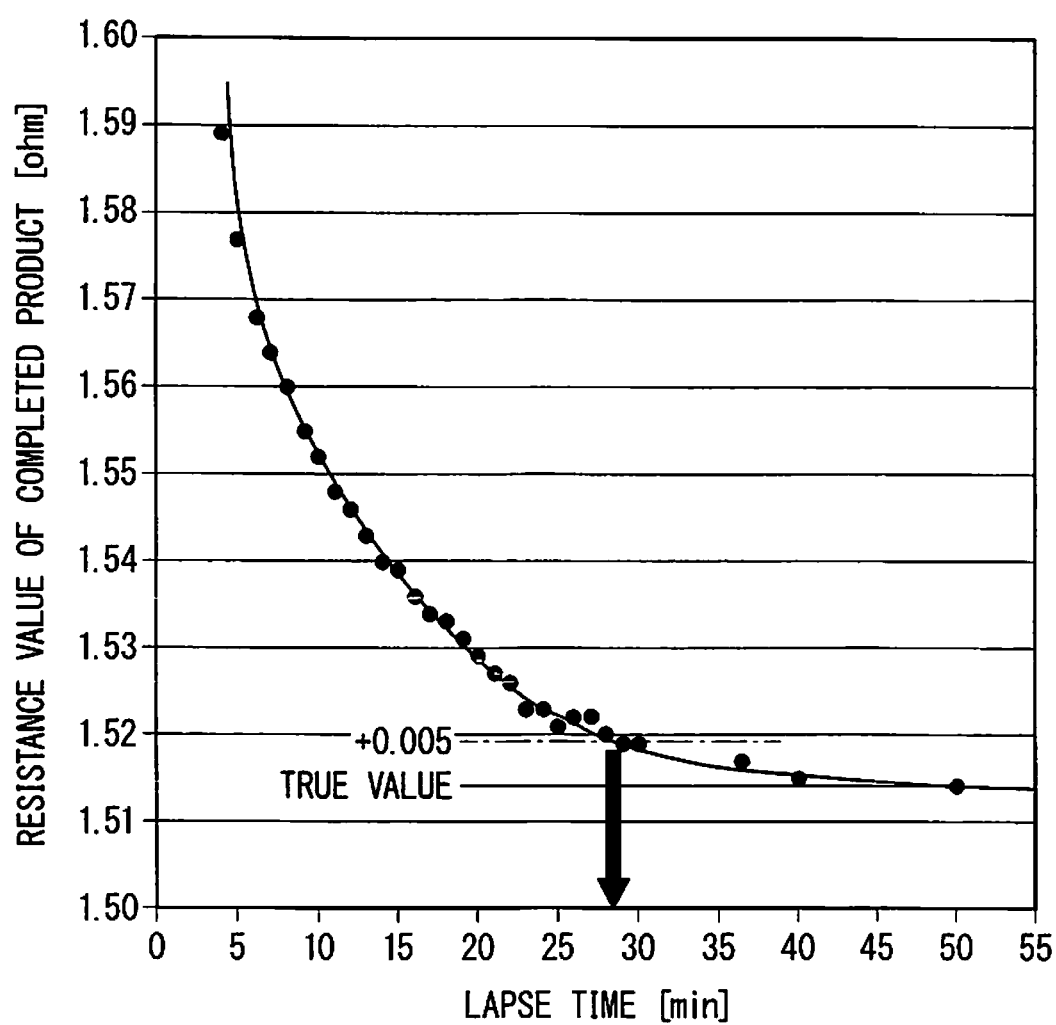

METHOD OF INSPECTING GAS SENSOR AND METHOD OF MANUFACTURING GAS SENSOR

BACKGROUND OF THE INVENTION

Field of the Invention

The present invention relates to an inspection method performed in a process of manufacturing a gas sensor.

Description of the Background Art

Conventionally, various measurement devices have been used for recognizing a concentration of a desired gas component in a measurement gas. For example, as a device for measuring an NOx concentration in a measurement gas such as a combustion gas, known is a gas sensor (an NOx sensor) provided with a sensor element which is made of a ceramic having an oxygen-ion conductivity such as zirconia ($ZrO_2$) (for example, refer to Japanese Patent Laid-Open No. 2006-284223). Such a sensor element of the gas sensor generally includes a plurality of electrode terminals on its surface to apply voltage, take out a detection signal, and supply electrical power to a heater (a resistance heating heater), for example.

In the meanwhile, a gas sensor includes a contact member into which the sensor element is inserted for holding the sensor element. For example, known is a gas sensor including a contact member which comprises a housing made of a ceramic (a ceramic housing) having a pair of housing members disposed to face each other to form an insertion opening into which a sensor element is inserted, a plurality of contact point members which are made up of a metal terminal to be attached to the housing members, and a plurality of lead wires connected to the contact point members for an electrical connection between the sensor element and outside (for example, refer to Japanese Patent No. 5082013).

In the gas sensor disclosed in Japanese Patent No. 5082013, the contact member holds the sensor element which is inserted into the insertion opening in a manner of contacting the contact point member and an electrode terminal, so that the electrical connection between the sensor element and the outside is obtained.

Moreover, also known is a method of manufacturing a circuit integrated gas sensor which prevents a disposal of a normal controller even when a sensor part has a defect (for example, refer to Japanese Patent Laid-Open No. 2007-225616).

In a technique disclosed in Japanese Patent Laid-Open No. 2007-225616, an inspection whether or not a detection element is normal is performed at the stage that a sensor intermediate assembly is formed before the detection element is integrated with the controller, and sensor intermediate assembly including an abnormal detection element is discarded, so that the expensive controller is prevented from being integrated with the abnormal detection element. In addition, the above inspection process is performed after confirming that a contact resistance of a lead terminal of the sensor intermediate assembly is at a level not having influence on an abnormality detection and a measurement of a characteristic information of the detection element, so that an accurate characteristic information for the detection element can be obtained, and a detection accuracy of an NOx sensor after completion can be secured.

In a case of a gas sensor disclosed in Japanese Patent No. 2006-284223, for example, the heater included in the sensor element is used for maintaining an operation temperature of the sensor element within a predetermined level. Since the operation characteristic of the sensor element varies depending on the temperature, an electrical resistance value of the heater (referred to as the heater resistance value) is one of the important characteristic values for the gas sensor. Therefore, for a mass-produced gas sensor, required is a securement that the heater resistance value falls within a predetermined range determined as a standard. Accordingly, an inspection whether or not the heater resistance value meets the standard is performed in the process of manufacturing the gas sensor.

However, only the evaluation of the heater resistance value on the sensor element itself before incorporated into the gas sensor is not preferable even when the heater resistance value of the sensor element can be accurately measured by reason that even when a defect occurs in an assembly process, the defect is not detected in the gas sensor which is finally obtained.

In the meanwhile, if only a gas sensor after assembled is subject to the inspection, the sensor element whose heater resistance value does not meet the standard is also provided to the assembly of the completed gas sensor, so that it is not preferable in point of productivity.

Accordingly, it is preferable to perform a two-stage inspection for the heater resistance value, that is, the inspection of the sensor element before incorporated into the gas sensor and the inspection of the gas sensor after assembled.

However, as disclosed in Japanese Patent No. 5082013, for example, in the gas sensor after assembled, the electrode terminal of the sensor element is electrically connected to the contact point member of the contact member and is not exposed to the outside in general. Accordingly, the inspection for the heater resistance value of the gas sensor after assembled needs to be performed via a lead wire connected to the contact member or via a connector, to which the lead wire is connected, for connecting an external equipment, differing from the inspection before incorporation which can be performed by directly accessing the electrode terminal of the sensor element.

The inventor of the present invention obtained a finding, as a result of earnest review, that when the heater resistance value is inspected, a determination of the presence or absence of an assembly defect of a gas sensor is enabled, more specifically, a determination of the presence or absence of a contact abnormality between the electrode terminal of the sensor element and the contact point member of the contact member is enabled, using the above difference between the subjects for the measurement, in addition to a determination whether or not the heater resistance value meets a predetermined standard.

Exemplified as a cause of the contact abnormality is that, for example, particles of talc (an insulating ceramic powder) which airtightly seal the sensor element in the gas sensor are sandwiched (caught) between the electrode terminal of the sensor element and the contact point member of the contact member, or that the electrode terminal is peeled out.

In the mass production process of the gas sensor, a large number of sensor elements are manufactured in one lot at the same time and each of them are provided to the assembly of the gas sensor, and a gas sensor whose heater resistance value does not meet the standard or a gas sensor which has the assembly defect needs to be reliably excluded from a shipping object.

Although Japanese Patent No. 2007-225616 discloses that the characteristic information is obtained by a performance inspection of the intermediate assembly, it does not disclose or suggest the inspection of the assembly state of the gas sensor using the heater resistance value.

SUMMARY OF THE INVENTION

The present invention relates to a method of inspecting a gas sensor, and particularly to an inspection method performed in a manufacturing process.

In the present invention, a gas sensor has a configuration that a sensor element is incorporated therein, and comprises: a first gas sensor constituting member having an insertion opening into which the sensor element is inserted; and a second gas sensor constituting member including the sensor element which partially protrudes from the second gas sensor constituting member. In the gas sensor, a part of the sensor element which protrudes from the second gas sensor constituting member is inserted into the insertion opening, so that the first gas sensor constituting member and the second gas sensor constituting member are integrated with each other. The sensor element includes a heater made up of a resistance heating member therein and also includes an electrode terminal for a heater in a surface thereof. The first gas sensor constituting member includes a contact point member which contacts the electrode terminal in a state where the sensor element is inserted into the insertion opening.

According to the present invention, a method of inspecting a presence or absence of an assembly defect of the gas sensor comprises steps of: determining an identification information enabling a unique identification of the sensor element; measuring a resistance value of the heater of the sensor element before incorporated into the gas sensor to obtain a first resistance value and associating the first resistance value with the identification information for the sensor element; measuring the resistance value of the heater via at least the contact point member, in a state where the first gas sensor constituting member and the second gas sensor constituting member are integrated with each other, to obtain a second resistance value and associating the second resistance value with the identification information for the sensor element; and comparing a difference value between the first and second resistance values associated with an identical identification information with a predetermined threshold value, and when the difference value exceeds the predetermined threshold value, determining that an assembly defect occurs in the gas sensor into which the sensor element, to which the identical identification information is provided, is incorporated.

According to the present invention, the gas sensor having the assembly defect in spite that the sensor element having the normal heater resistance value is incorporated therein can be excluded from the shipping object.

Preferably, the second gas sensor constituting member is formed with a plurality of annularly-mounted members including a ceramic powder compact annularly mounted to the sensor element.

In this case, the gas sensor which has a defect that a ceramic powder is sandwiched between the electrode terminal and the contact point member can be excluded from the shipping object.

Preferably, in the gas sensor, an outer tube covering the first gas sensor constituting member is laser-welded to the second gas sensor constituting member being integrated with the first gas sensor constituting member, a measurement of the resistance value of the heater for obtaining the first resistance value is performed in air at room temperature, and a measurement of the resistance value of the heater for obtaining the second resistance value is performed in air at the time when thirty minutes has passed after completing the laser welding of the outer tube.

In this case, even when the gas sensor is heated by the laser welding, the measurement temperature in the two measurement processes can be substantially the same as each other, so that the determination of the assembly defect can be accurately performed.

Accordingly, an object of the present invention is to provide a method of inspecting a gas sensor capable of determining a presence or absence of an assembly defect of an individual gas sensor in a mass-production process of the gas sensor.

BRIEF DESCRIPTION OF THE DRAWINGS

FIG. 4 is a drawing for describing details of an electrode terminal 13 of a sensor element 1.

FIG. 7 is a front view of an end part 20A on a side of an insertion opening 23 of the contact member 20.

FIG. 9 is a graph showing a temporal change of a heater resistance value of a heater 70 included in the sensor element 1 incorporated into the gas sensor 100 when the gas sensor 100 is completed and stored at room temperature.

DESCRIPTION OF THE PREFERRED EMBODIMENTS

<Configuration of Gas Sensor>

Figure 1:
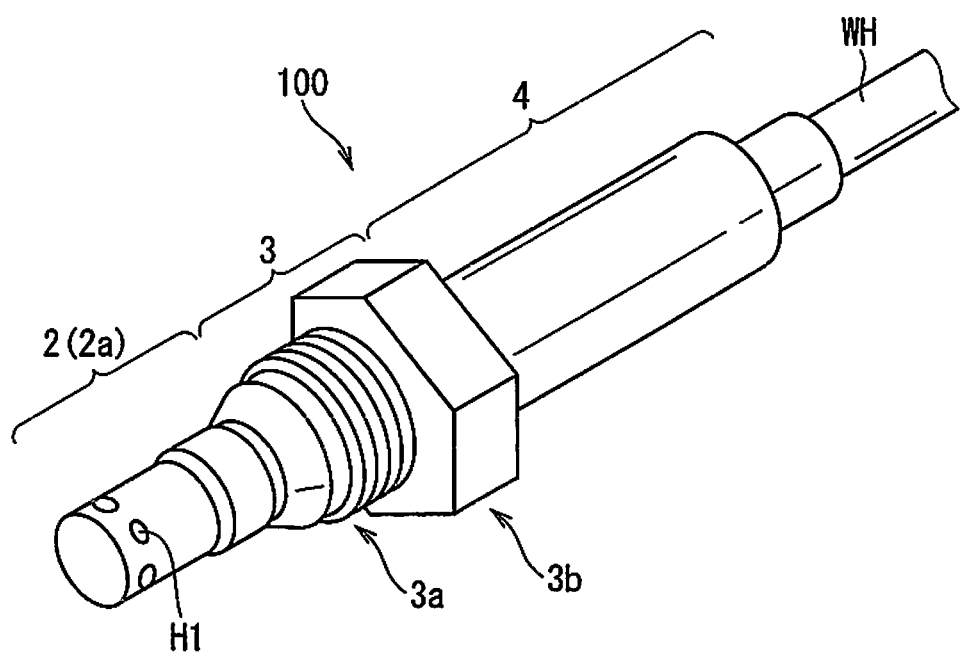
FIG. 1 is a perspective view of an external appearance of a gas sensor 100.
Figure 2A:
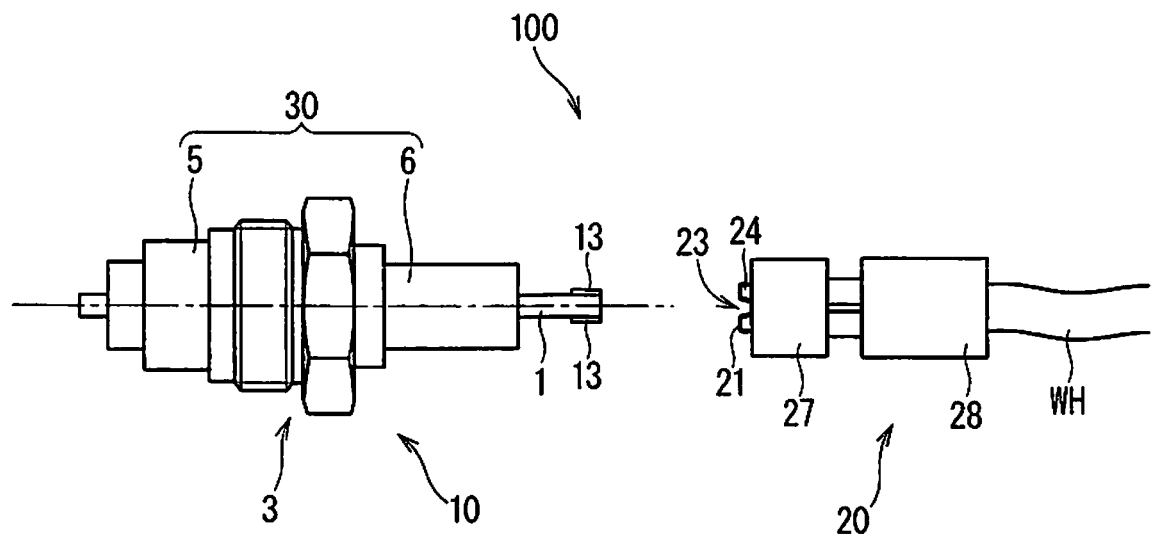
FIG. 2A and FIG. 2B are drawing illustrating a state of assembling the gas sensor 100.
Figure 2B:
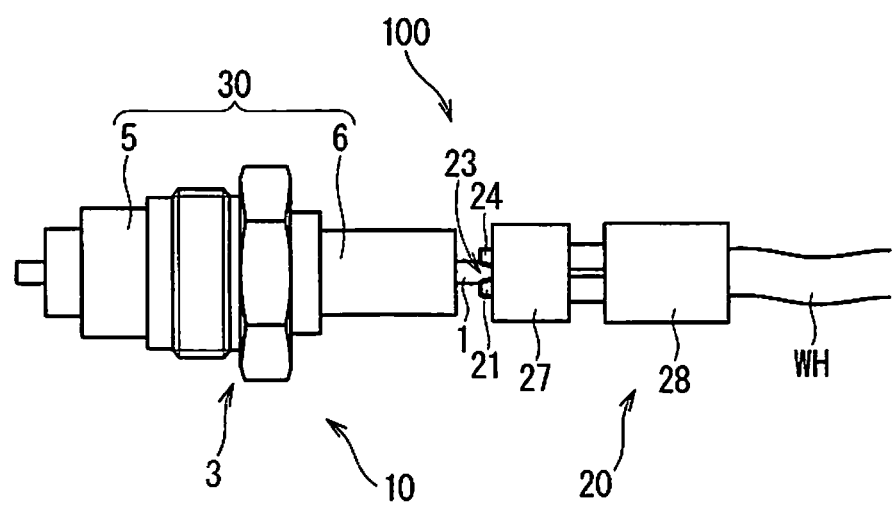
Figure 3:
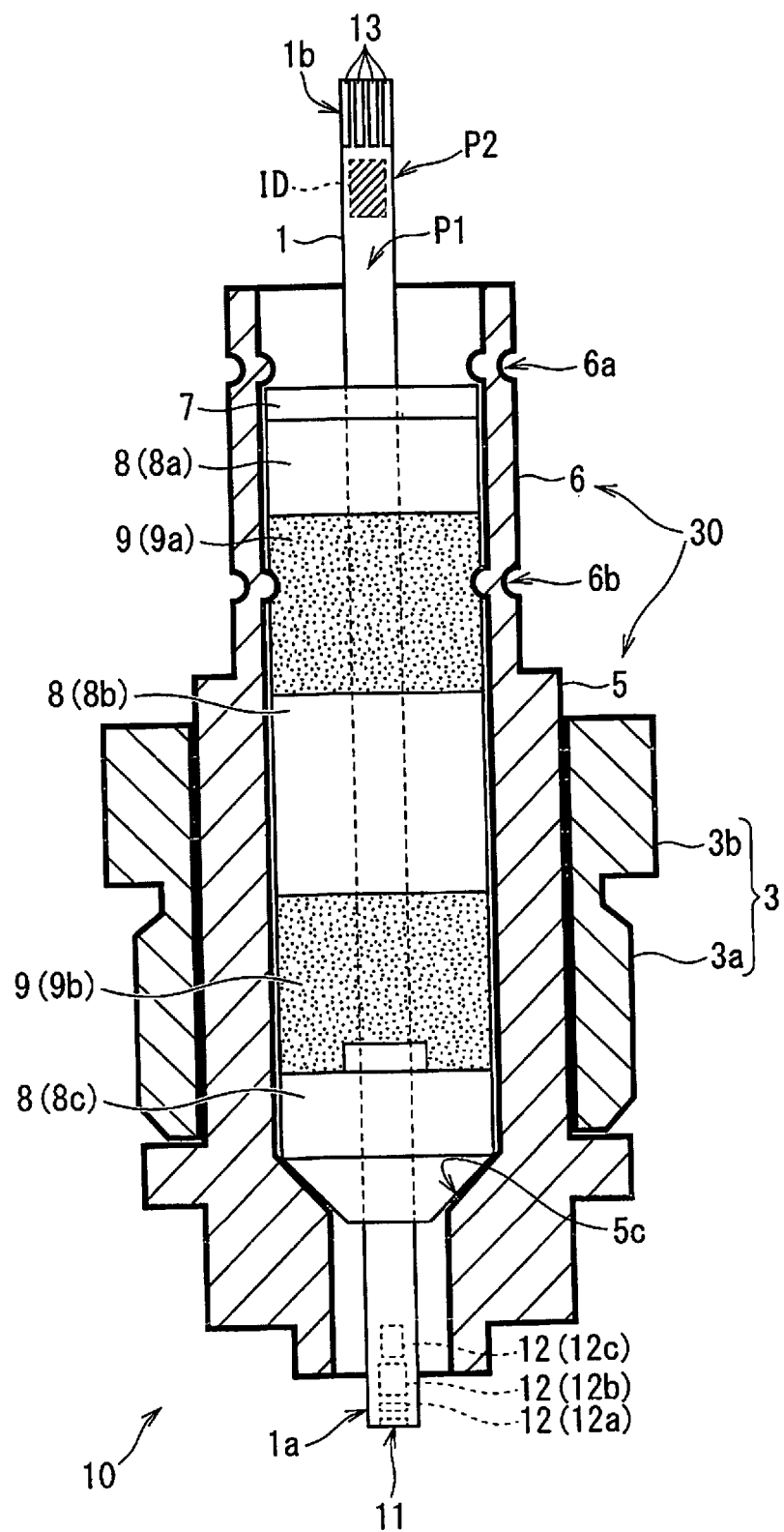
FIG. 3 is a partial cross-sectional view showing a more detailed configuration of a gas sensor body 10.

FIG. 1 is a perspective view of an external appearance of a gas sensor 100 which is subject to an inspection in the present embodiment. FIG. 2A and FIG. 2B are drawing illustrating a state of assembling the gas sensor 100. FIG. 2A illustrates a state before assembly and FIG. 2B illustrates a state after assembly. However, an element protection cover 2 and an outer tube 4 are omitted in FIG. 2A and FIG. 2B. FIG. 3 is a partial cross-sectional view showing a more detailed configuration of a gas sensor body 10.

The gas sensor 100 serves to detect a predetermined gas component (an object gas component) in a gas (a measurement gas) which is subject to a measurement with a sensor element 1 (refer to FIG. 2A, FIG. 2B, and FIG. 3) included therein, and further measure a concentration of the object gas component. Examples of the object gas component include NOx.

The sensor element 1 is an elongated columnar or thin-plate like member including, as a main constituent material, oxygen-ion conductive solid electrolyte ceramic such as zirconia. The sensor element 1 comprises a gas inlet 11 which opens in a first tip portion 1a, which is located in a lowest end part in FIG. 3, includes a closed space 12 (a buffer space 12a, a first internal space 12b, and a second internal space 12c) or the like, in an inner portion thereof, and further has various electrodes, heater patterns, and wiring patterns in a surface and inner portion of an element body. The gas inlet 11, the buffer space 12a, the first internal space 12b, and the second internal space 12c are arranged in this order along a longitudinal direction of the sensor element 1 and are communicated with each other via diffusion-controlling parts.

In the sensor element 1, an inspected gas introduced from the gas inlet 11 to the closed space 12 is reduced or decomposed in the closed space 12 (for example, the second internal space 12c) and oxygen ion is thereby generated. In the gas sensor 100, substantially, a concentration of the gas component is obtained based on a fact that an amount of an oxygen-ion current flowing between predetermined electrodes provided in the gas sensor 100 is proportional to a concentration of the gas component in the inspected gas.

A surface which faces front in FIG. 3 and a surface which is parallel to it are referred to as a main surface P1, and a surface which is perpendicular to the main surface P1 and extends along the longitudinal direction and a surface which is parallel to it are referred to as a side surface P2. Both the main surface P1 and the side surface P2 extend in the longitudinal direction of the sensor element 1, and a width of the main surface P1 is larger than that of the main surface P2.

In the present embodiment, as shown in FIG. 3, an element identification mark ID is provided on at least one main surface P1 of the sensor element 1. The element identification mark ID is a mark relating to information for uniquely identifying an individual of each sensor element 1 (the element identification information). The element identification information is made up of character string by arranging a number or a code, for example, in accordance with a predetermined rule, and a unique element identification information is determined for each sensor element 1. A position in which the element identification mark ID shown in FIG. 3 is just an example, so that the actual position is not limited to the above exemplification.

As the element identification mark ID, a character string itself of the element identification information may be provided, or an element identification information which is converted into a bar code or a two dimensional code may also be provided. The element identification mark ID may be provided by a known method such as printing, laser baking, drawing, or engraving, for example, after manufacturing the sensor element 1.

In the present embodiment, the element identification information obtained by reading the element identification mark ID with a predetermined reading means is used in a process of inspecting the gas sensor 100. The detail is described hereinafter. The reading means is appropriately selected from a camera or a scanner, for example, in accordance with a form of the element identification mark ID.

As shown in FIG. 1, an outer side portion of the gas sensor 100 is mainly constituted by an element protection cover (a first cover) 2, a fixing bolt 3, and an outer tube (a second cover) 4.

The element protection cover 2 is an exterior member with an approximately-cylindrical shape for protecting the portion of the sensor element 1 which directly comes into contact with the measurement gas during usage, specifically, for protecting the first tip portion 1a including the gas inlet 11 and the closed space 12, for example.

More specifically, the element protection cover 2 has a double-layer structure of an outside cover 2a and an inside cover (not shown). Each of the outside cover 2a and inside cover has a circular and bottomed shape on one side and has a plurality of through holes through which a gas passes in the side portion. FIG. 1 illustrates through holes H1 provided in the outside cover 2a, which are merely an example. The position and number of through holes arranged may be appropriately determined in consideration of how a measurement gas flows into the element protection cover 2.

The fixing bolt 3 is an annular member used when the gas sensor 100 is fixed at a measurement position. The fixing bolt 3 includes a threaded bolt portion 3a and a held portion 3b to be held when the bolt portion 3a is screwed. The bolt portion 3a is screwed with a nut portion provided at a position at which the gas sensor 100 is mounted. For example, the bolt portion 3a is screwed with a nut portion provided in the car exhaust pipe, whereby the gas sensor 100 is fixed to the exhaust pipe such that the element protection cover 2 side thereof is exposed in the exhaust pipe.

The outer tube 4 is a cylindrical member that protects other portion of the gas sensor 100. A wire harness WH constituting the contact member 20 extends from an end of the outer tube 4.

As shown in FIG. 2B, the gas sensor 100 has a structure that the gas sensor body 10 (the second gas sensor constituent member) and the contact member 20 (the first gas sensor constituent member) are integrated with each other in an inner portion thereof.

The contact member 20 is made up mainly of a plurality of contact point members 21, the wire harness WH for housing a plurality of lead wires whose one end side is connected to the contact point member 21, a second housing 24, which is made of a ceramic, for holding the sensor element 1 in a manner that the sensor element 1 is inserted into an insertion opening 23 via the contact point member 21, a swaging ring 27 which is provided for fixing the second housing 24 into which the sensor element 1 is inserted from an outer periphery, and a grommet (a rubber plug) 28 in which the lead wires are airtightly inserted through. A connector not shown in the drawings for electrically connecting the gas sensor 100 to an external drive control unit is provided in an opposite end of the wire harness WH.

As shown in FIG. 2B, a tip portion (a protruding portion from a tubular body 30) including the electrode terminal 13 of the sensor element 1 comprised in the gas sensor body 10 is inserted into the insertion opening 23 of the second housing 24 comprised in the contact member 20, and the sensor element 1 is held in the second housing 24 via the contact point member 21, so that the gas sensor 100 is integrally formed.

In the meanwhile, as shown in FIG. 2A, in the gas sensor body 10, the sensor element 1 being a gas detection unit is housed in the tubular body 30 being the cylindrical housing member except both end parts thereof. The tubular body 30 is formed of a first housing 5 being a metal cylindrical member and an inner tube 6 being a metal cylindrical member, integrated with each other by welding. Accordingly, the tubular body 30 is also referred to as the inner tube welded product. The fixing bolt 3 is provided in an outer periphery of the tubular body 30.

More particularly, as shown in FIG. 3, inside the gas sensor body 10, a washer 7, three ceramic supporters 8 (8a, 8b, and 8c), and two powder compacts 9 (9a and 9b) are each annularly mounted to the part of the sensor element 1 other than the first tip portion 1a including the gas inlet 11 or the like and a second tip portion 1b including the electrode terminal 13, which is a connection terminal with the contact point member 21 included in the contact member 20 or the like, such that the sensor element 1 is positioned about the axis. A ceramic supporter 8 is a ceramic insulator. Meanwhile, the powder compact 9 is obtained by shaping ceramic powders such as talc. In the following description, the washer 7, the ceramic supporters 8, and the powder compacts 9 are collectively referred to as annularly-mounted members, in some cases, and an assembly in a state that these annularly-mounted members are annularly mounted to the sensor element 1 is referred to as the post-annularly-mounted assembly, in some cases.

Moreover, the tubular body 30 is annularly mounted to an outer periphery of the washer 7, the ceramic supporters 8 (8a, 8b, and 8c), and the powder compacts 9 (9a and 9b).

As described above, the tubular body 30 is integrally formed by welding one end of the inner tube 6 to the first housing 5. The first housing 5 and the inner tube 6 have substantially the same inside diameter and are connected coaxially. An inside diameter of the tubular body 30 is set to be larger than designed values of maximum outside diameters of the respective annularly-mounted members.

The first housing 5 is provided with a tapered portion 5c at one end side of the inside thereof. One end sides of the post-annularly-mounted assembly are engaged with an inside of the tubular body 30 by the tapered portion 5c. In a position of the inner tube 6 right above the washer 7 and a position of the inner tube 6 at a side of the powder compacts 9a, respectively, concave portions 6a and 6b concaved inwardly are formed. Other end sides of the post-annularly-mounted assembly are engaged with the inside of the tubular body 30 by the concave portions 6a and 6b.

More particularly, the powder compact 9 is compressed after being annularly mounted, and is thereby attached firmly to the sensor element 1. The concave portions 6a and 6b are provided after compressing the powder compact 9. As a result that the firm attachment of the powder compact 9 to the sensor element 1 is achieved, in the tubular body 30, the sensor element 1 is fixed, and a sealing between the first tip portion 1a side including the gas inlet 11 or the like and the second tip portion 1b including the electrode terminal 13 or the like in the sensor element 1 is achieved. According to the above configuration, airtightness between a measurement gas space including the inspected gas (the measurement gas) with which the first tip portion 1a of the sensor element 1 contacts and a reference gas space including a reference gas such as the atmosphere, for example, with which the second tip portion 1b contacts is secured. The concave portions 6a and 6b are provided to maintain the compression state of the powder compact 9.

FIG. 4 is a drawing for describing details of the electrode terminal 13 of the sensor element 1. The plurality of electrode terminals 13 are provided in the side of the second tip portion 1b in the main surface P1 of the sensor element 1. In the present embodiment, as illustrated by arrows AR1 and AR2 in FIG. 4, each of the two main surfaces P1 (P1a and P1b) of the sensor element 1 facing each other are provided with the four electrode terminals 13, that is, the eight electrode terminals 13 in total. Specifically, electrode terminals 13a to 13d are provided in the one main surface P1a, and electrode terminals 13e to 13h are provided in the other main surface P1b. Particularly, the electrode terminals 13f to 13h in the above electrode terminals 13 are also referred to as H+ electrode, H− electrode, and Ht electrode, respectively.

Figure 5:
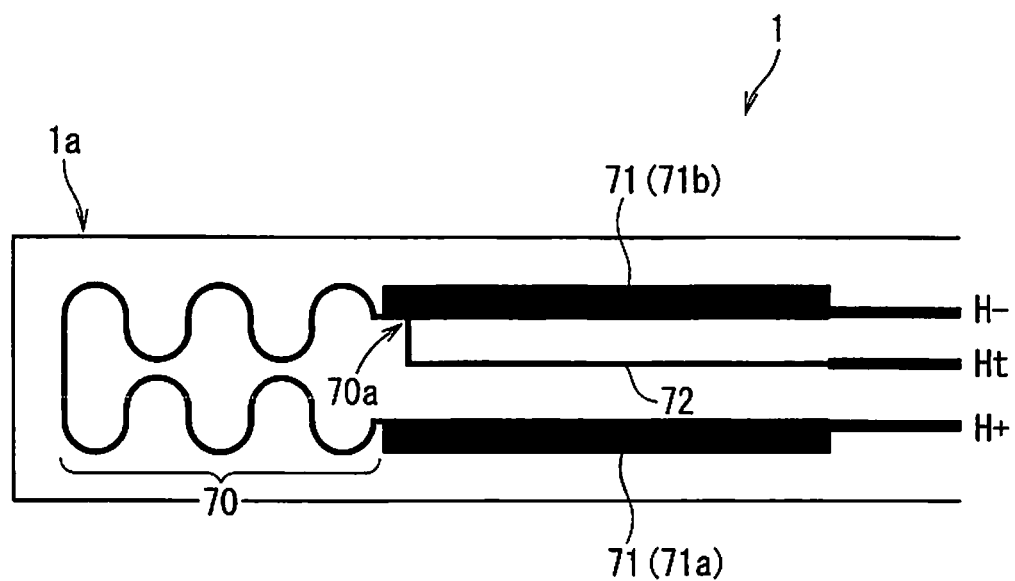
FIG. 5 is a drawing exemplifying a heater structure included in the sensor element 1.

FIG. 5 is a drawing exemplifying a heater structure included in the sensor element 1. The sensor element 1 comprises therein a heater 70 and a pair of heater leads 71 (71a and 71b) connected to both ends of the heater 70. The heater 70 is a resistance heating element which generates heat when electrical power is supplied from outside of the sensor element 1 via the heater lead 71 which is an energizing path. The heater 70 can be formed of platinum, for example. The heater 70 is embedded in the side of the first tip portion 1a of the sensor element 1. An insulating layer made of alumina, for example, is formed above and below the heater 70 and heater lead 71 with a view to obtaining an electric insulation with an oxygen-ion conductive solid electrolyte.

The heater lead 71a and the heater lead 71b are provided to have substantially the same shape, that is to say, to have the same resistance value as each other. The one heater lead 71a is connected to the H+ electrode (the electrode terminal 13f) inside the sensor element 1, and the other heater lead 71b is connected to the H− electrode (the electrode terminal 13g) inside the sensor element 1.

Furthermore, a resistance detection lead 72 is provided in a manner of being lead from a connection part 70a of the heater 70 and the heater lead 71b. A resistance value of the resistance detection lead 72 can be ignored. The resistance detection lead 72 is connected to the Ht electrode (the electrode terminal 13h) inside the sensor element 1.

In the sensor element 1, electrical current is applied between the H+ electrode and the H− electrode heat with the heater 70, so that the closed space 12 and a surrounding area thereof (and the electrodes provided in each of them) can be heated to and kept at a predetermined temperature. The oxygen-ion conductivity of the solid electrolyte constituting the sensor element 1 is increased by the heat generation of the heater 70.

Since the heater lead 71a and the heater lead 71b have the same resistance value as each other and the resistance value of the resistance detection lead 72 can be ignored, a resistance value of the heater 70 (the heater resistance value) $R_H$ is calculated by the following equation when a resistance value between the H+ electrode and the Ht electrode is represented by $R_1$ and a resistance value between the H− electrode and the Ht electrode is represented by $R_2$:

$$R_H = R_1 - R_2 \qquad (1)$$

As described hereinafter, the heater resistance value calculated by the equation (1) is subject to the inspection in a process of manufacturing the gas sensor 100 as the mass-produced product and shipping it according to the present embodiment.

Figure 6A:
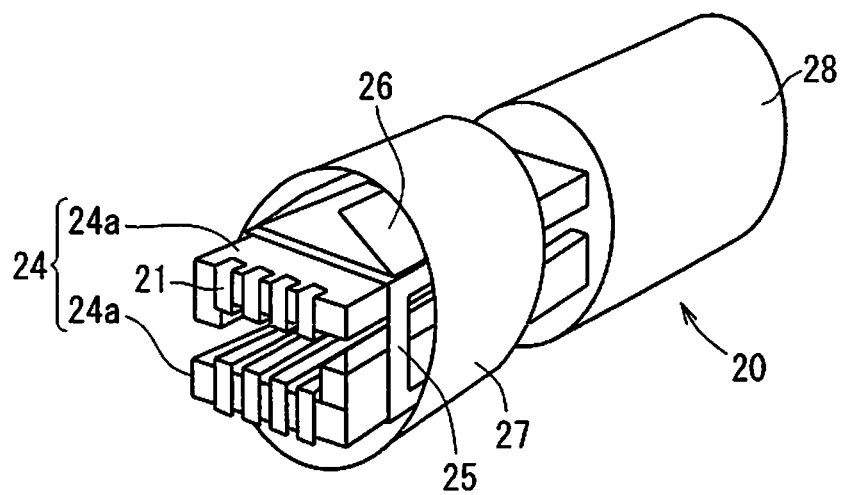
FIG. 6A, FIG. 6B, and FIG. 6C are drawings for describing a more detailed configuration of a contact member 20.
Figure 6B:
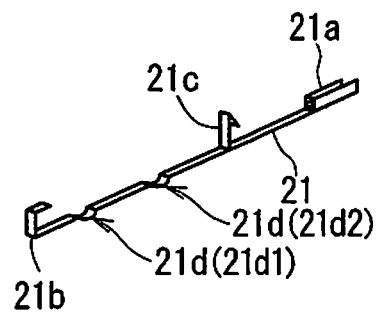
Figure 6C:
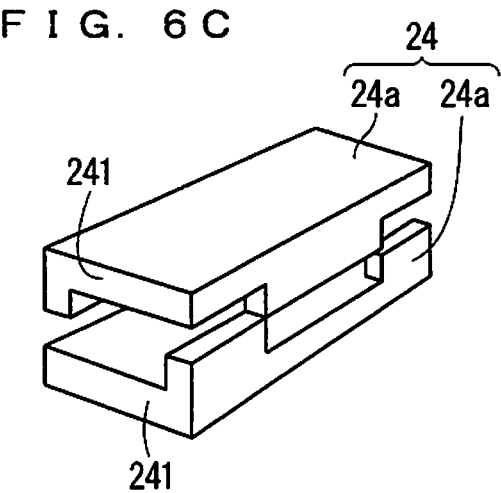

FIG. 6A, FIG. 6B, and FIG. 6C are drawings for describing a more detailed configuration of the contact member 20. FIG. 6A is a perspective view of the contact member 20, and FIGS. 6B and 6C are perspective views of the contact point member 21 and the second housing 24 constituting the contact member 20, respectively. FIG. 7 is a front view of the end part 20A on a side of the insertion opening 23 of the contact member 20.

The contact member 20 has a configuration that the plurality of contact point members 21 which are connected to the lead wire inserted through the grommet 28 are hooked on each of the pair of the housing members 24a which face each other and constitute the second housing 24, and a metal fixture 25 including a pressing spring 26 and the swaging ring 27 are attached to an outer periphery of the second housing 24.

As shown in FIG. 7, the end part 20A of the contact member 20 has a point-symmetric configuration. FIG. 7 exemplifies a case where four out of eight contact point members 21 (211 to 218) are provided in each housing member 24a corresponding to the arrangement and the number of the electrode terminals 13 in the sensor element 1. When the gas sensor body 10 and the contact member 20 are integrated with each other, each of the electrode terminals 13 of the sensor element 1 is connected to the different contact point member 21.

Each of the contact point member 21 includes, as shown in FIG. 6B, a crimping part 21a to which a tip of the lead wire is connected, a first hooking part 21b and a second hooking part 21c hooked on predetermined positions of the housing member 24a, and a protruding part 21d (21d1 and 21d2) which biases the sensor element 1 in a state where the sensor element 1 is inserted into the insertion opening and also serves as a contact point contacting the electrode terminal 13 of the sensor element 1.

The connection between the lead wire and the contact point member 21 is achieved by swaging the crimping part 21a from outside in a state where the tip of the lead wire is held by the crimping part 21a.

The first hooking part 21b of the contact point member 21 is hooked on a first hooked part 241 provided in one end of the housing member 24a. Accordingly, each shape of the first hooking part 21b and the first hooked part 241 is designed so that the hooking state is successfully maintained. That is to say, the first hooking part 21b has been processed to have a shape along a side cross-sectional shape of the first hooked part 241. In the meanwhile, the second hooking part 21c is hooked on the housing member 24a by being inserted into a second hooked part, not shown in the drawings, provided in a central part of the housing member 24a.

The housing members 24a have substantial the same cross-sectional shape as each other and are arranged apart from each other so that a rectangular space in a cross-sectional view which secures the insertion opening 23 is formed therebetween. Accordingly, as shown in FIG. 7, a gap 24b is provided in each end of the two housing member 24a. In other words, each housing member 24a has such a shape that a rectangular housing in a cross-sectional view having a space inside is divided into two halves. Since each housing member 24a is attached in the above manner, a neighborhood of a tip of the housing member 24a (a neighborhood of the end of the insertion opening 23) can be displaced upward or downward within a predetermined range upon receiving an external force directed from an inner side of the insertion opening 23 toward a vertical direction in FIG. 7. Then, these one pair of the housing members 24a receives the external force and thereby holds the sensor element 1 in the insertion opening 23, so that the sensor element 1 is fixed to the contact member.

A pressure spring 26 is a plate spring member having a trapezoidal shape in a cross-sectional view without an upper base, and when the external force acts on its free end 261, elastic force is generated as its restoring force.

The metal fixture 25 has a role of fixing the pressure spring 26, and also has a role of maintaining the state of attaching the second housing 24, more specifically, the state of forming the insertion opening 23 until the sensor element 1 is hold and fixed. In other words, the metal fixture 25 is a restraining member which restrains the pair of housing members 24a within the predetermined position so that the state of forming the insertion opening 23 is maintained. As the metal fixture 25 is attached together with the second housing 24, a misalignment between each contact point member 21 (in more detail, the protruding part 21d1 thereof) of the sensor element 1 and the corresponding electrode terminal 13 is prevented when the sensor element 1 is fixed. That is to say, the metal fixture 25 also has a role of restraining the arrangement range of the sensor element 1 at the time when holding and fixing the sensor element 1.

The swaging ring 27 is swaged in a state where the sensor element 1 is inserted into the insertion opening 23 of the second housing 24 at the time when the gas sensor body 10 and the contact member 20 are integrated with each other. That is to say, the swaging ring 27 is shrunk and deformed by the external force. Accordingly, an interval of the insertion opening 23 of the second housing 24 is narrowed, and the sensor element 1 is biased by the contact point member 21 included in each housing member 24a from two directions, that is, upward and downward directions. That is to say, achieved is the state where the sensor element 1 is held and fixed by the pair of housing members 24a. At this time, the protruding part 21d1 of each contact point member 21 contacts the corresponding electrode terminal 13, so that in the gas sensor 100, the electrical conduction between the sensor element 1 and the outside is achieved via the lead wire connected to the contact point member 21 and further a connector, not shown in the drawings, connected to the lead wire. The protruding part 21d1 has a surface contact with the electrode terminal 13 within a range of approximately 0.5 mm φ.

<Summary of Process of Mass-Producing Gas Sensor and Heater Resistance Inspection>

Figure 8:
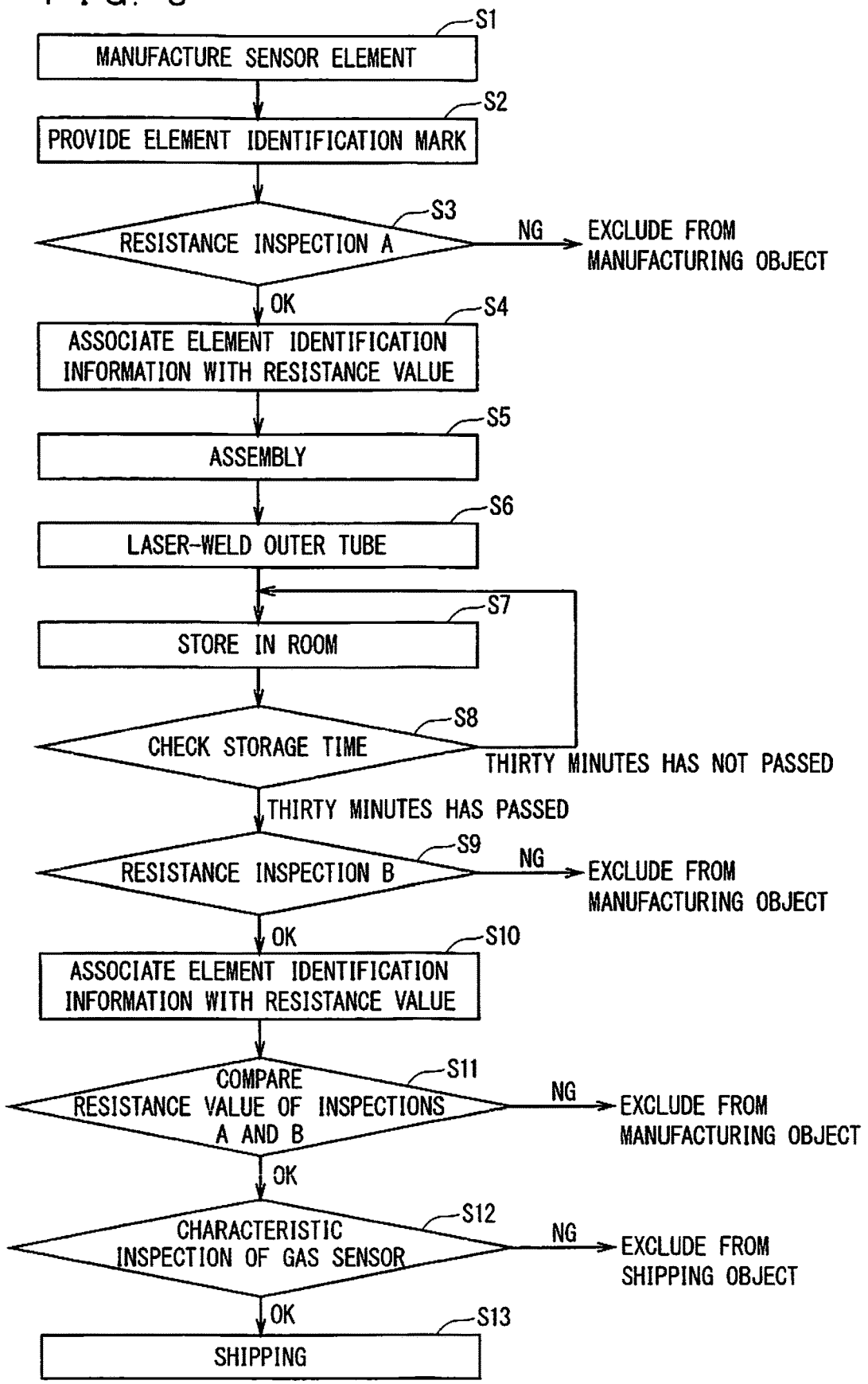
FIG. 8 is a drawing illustrating a procedure of manufacturing and shipping the gas sensor 100 as a mass-produced product, focusing on a process related mainly to a heater resistance inspection.

FIG. 8 is a drawing illustrating a procedure of manufacturing and shipping the gas sensor 100 according to the present embodiment as the mass-produced product, focusing on the process related mainly to the heater resistance inspection.

The sensor element 1 is manufactured in advance when the gas sensor 100 is manufactured (a step S1). The sensor element 1 is manufactured by a so-called a green sheet process. That is to say, in manufacturing the sensor element 1, prepared firstly are a plurality of ceramic green sheets including an oxygen-ion conductive solid electrolyte ceramic such as zirconia ($ZrO_2$) as a main raw material. Subsequently, a predetermined process such as punching processing and a printing of an electrode or a wiring pattern, for example, are performed on the ceramic green sheets in a predetermined manner, and a predetermined number of the processed ceramic green sheets are laminated in a predetermined order. A laminate of the ceramic green sheets obtained by the above process is cut into predetermined-sized laminated bodies. The laminated body after the cutting process is baked, and the sensor element 1 is thereby manufactured.

According the above process, a large number of sensor elements 1 are manufactured at the same time, however, they have the same appearance, so that they are not distinguished from each other in appearance. In the present embodiment, the element identification information for uniquely identifying the individual sensor element 1 is determined for each sensor, and the element identification mark ID is provided in the predetermined position of the main surface P1 of the sensor element 1 based on the element identification information (a step S2). As described above, the embodiment of the element identification mark ID may be appropriately selected from a character string, a bar code or a two dimensional code, for example, and the method of providing the element identification mark ID may be appropriately selected from various known methods such as printing, laser baking, drawing, or engraving, for example.

The respective sensor elements 1 to which the element identification mark ID has been provided are sequentially targeted to a first inspection of the heater resistance value (referred to as a resistance inspection A) (a step S3).

The resistance inspection A is performed based on the equation (1). That is to say, the resistance value $R_1$ between the H+ electrode and the Ht electrode and the resistance value $R_2$ between the H− electrode and the Ht electrode are measured, and it is determined whether or not the heater resistance value $R_H$ calculated from those values by the equation (1) falls within a predetermined range of value determined as the standard. The heater resistance value $R_H$ obtained in the resistance inspection A is particularly defined as a heater resistance value $R_{HA}$.

The measurement of the resistance values $R_1$ and $R_2$ of the sensor element 1 in the resistance inspection A is performed by one measuring equipment having a prove being able to contact the H+ electrode, the H− electrode, and the Ht electrode (the electrode terminals 13f to 13h) in the same condition all the time under an environment of keeping the temperature of the sensor element 1 (the element temperature in measurement) constant. In the present embodiment, the element temperature in measurement is set to the room temperature (25° C.) and the resistance inspection A is performed in the air (atmosphere).

The rejected sensor element 1 whose heater resistance value $R_{HA}$ measured in the resistance inspection A does not meet the predetermined standard (for example, the predetermined resistance value range) (NG in the step S3) is excluded from a manufacturing object of the gas sensor 100.

When the standard of the heater resistance value $R_{HA}$ includes the resistance value range, the resistance value range is preferably set more strict than the range of the resistance value allowed in the actual use of the gas sensor 100. The reason is that it is anticipated that the range of the heater resistance value in the gas sensor 100 which is finally obtained by incorporating the sensor element 1 is set as the range of the resistance value allowed in the actual use of the gas sensor 100.

With regard to the accepted sensor element 1 whose heater resistance value $R_{HA}$ measured in the resistance inspection A meets the predetermined standard (OK in the step S3), the element identification information and the heater resistance value $R_{HA}$ of the accepted element 1 are associated with each other (a step S4). The above association can be performed in various manners within a scope that it can be referred in the following step. For example, the associated information may be recorded in a predetermined recording medium as an electronic data, may be recorded in or outputted to a paper medium, or may be provided anew to the sensor element 1 using laser baking or drawing, for example. Various information associated with the element identification information are collectively referred to as an associated information in the following description.

The sensor element 1 on which the association has been performed is subject to an assembly step of assembling the gas sensor 100 (a step S5). Note that, in FIG. 8 and the subsequent description, fixing of the outer tube 4 to the tubular body 30 performed by laser welding, which is finally performed in the assembly step of the gas sensor 100, is treated as a process separated from the overall preceding assembly steps (the step S5) for convenience. In other words, the assembly step in FIG. 8 and the subsequent description means a step up to the integration of the gas sensor body 10 and the contact member 20.

The assembly of the gas sensor 100 is achieved by assembling the gas sensor body 10 including the sensor element 1 and the contact member 20 via the independent steps, respectively, and subsequently, integrating them finally. When the individual gas sensor 100 is assembled in the assembly step, the element identification mark ID of the sensor element 1 to be incorporated is read in advance, and the element identification information and the information associated therewith for the incorporated sensor element 1 is enabled to be appropriately used in relation to the gas sensor 100 finally obtained.

In assembling the gas sensor body 10, firstly, the annually-mounted members (the washer 7, the ceramic supporter 8, and the powder compact 9) are annually mounted to the sensor element 1. Subsequently, the tubular body 30 (the first housing 5 and the inner tube 6) is annularly mounted to the outer periphery of the annularly-mounted members, and finally, the first cover and the fixing bolt 3 are attached to the tubular body 30. The gas sensor body 10 is thereby assembled.

In assembling the contact member 20, one ends of the lead wires inserted through the grommet 28 in advance are attached to the plurality of contact point members 21 using a method such as crimping, for example. Subsequently, each contact point member 21 is hooked on each of the pair of the housing members 24a constituting the second housing 24, and then, the metal fixture 25 and the swaging ring 27 are annularly mounted to the outer periphery of the second housing 24. In addition, the lead wires are inserted through the outer tube 4 and the other end of the lead wires are connected to a connector not shown in the drawings. The contact member 20 is thereby assembled.

As described above, since a large number of sensor elements 1 are manufactured at the same time, the gas sensor body 10 and the contact member 20 are manufactured so that the number of them matches the number of the sensor elements.

When the gas sensor body 10 and the contact member 20 are integrated, at first, as shown in FIG. 2B, the tip portion (the protruding portion from the tubular body 30) including the electrode terminal 13 of the sensor element 1 included in the gas sensor body 10 is inserted into the insertion opening 23 of the second housing 24 formed in the contact member 20. The sensor element 1 is thereby held by the second housing 24 (the pair of housing members 24a). After the insertion, the swaging ring 27 is swaged, so that the contact point member 21 of the second housing 24 (the protruding part 21d of the contact point member 21 in more detail) is biased, and the state that the sensor element 1 is held by the second housing 24 is maintained. Accordingly, the gas sensor body 10 and the contact member 20 are integrated with each other.

At this time, the protruding part 21d1 which is located in a position closer to the first hooking part 21b in the two protruding parts 21d of each of the contact point member 21 contacts the electrode terminal 13 of the sensor element 1. The sensor element 1 and the lead wire of the contact member 20 are electrically connected to each other by the contact between the electrode terminal 13 and the protruding part 21d1, and the electrical connection of the sensor element 1 and the outside of the gas sensor 100 is achieved via the lead wire and the connector.

After integrating the gas sensor body 10 and the contact member 20 in the manner described above, the outer tube 4 through which the lead wire has been inserted in advance is fixed to the tubular body 30 using the laser welding (a step S6). The gas sensor 100 is thereby completed.

With regard to the gas sensor 100 after assembled, since the sensor element 1 cannot be seen from outside, the element identification mark and the other information provided to the sensor element 1 may be again provided to the outer tube 4 using a method such as a laser marking, for example, at an appropriate timing before or after welding the outer tube 4 to the tubular body 30.

Various inspection steps including the inspection of the heater resistance value are performed on the gas sensor 100 which is completed by the procedure described above, however, prior to the inspection steps, the gas sensor 100 is stored in a predetermined (indoor) storage area at the room temperature until a certain period of time has passed (a step S7). The storing is conducted for the purpose of cooling the gas sensor 100, particularly the sensor element 1 inside the gas sensor 100.

Prior to the storing of the gas sensor 100, a termination time of the laser welding in each gas sensor 100 is associated with the element identification information of the sensor element 1 incorporated into the gas sensor 100. The association can also be performed in a manner similar to the association of the heater resistance value $R_{HA}$ described above. For example, the associated information may be recorded as an electronic data, may be recorded in or outputted to a paper medium, or may be laser-marked on the outer tube 4.

When the outer tube 4 is laser-welded, the gas sensor 100 is heated by the laser, so that the temperature of the sensor element 1 also rises. Accordingly, the temperature of the heater 70 inside the sensor element 1 also rises. Since the resistance value of the resistance heating element constituting the heater 70 changes depending on the temperature, when the heater resistance value is measured in such a state where the temperature rises, the value differs from the measurement value at the time of the resistance inspection A even when the heater 70 is in a normal state. In the case that there is a difference in the heater difference value according to such an element temperature, a presence or absence of the change in the heater resistance value caused by the assembly process cannot be determined. Therefore, the gas sensor 100 is stored for a certain period of time so that the sensor element 1 constituting the gas sensor 100 is cooled to the element temperature in measurement.

FIG. 9 is a graph showing a temporal change of the heater resistance value $R_H$ (shown as "resistance value of completed product" in FIG. 9) of the heater 70 included in the sensor element 1 incorporated into the gas sensor 100 when the gas sensor 100 is completed (that is to say, the laser welding of the outer tube 4 is finished) and stored at the room temperature (approximately 25° C.), which the inventor of the present invention has experimentally confirmed in advance.

As shown in FIG. 9, the heater resistance value $R_H$ which has increased after the laser welding of the outer tube 4 gradually decreases as time proceeds, and keeps an approximately certain value (shown as "true value" in FIG. 9) after a lapse of forty minutes. Accordingly, it is deemed that the gas sensor 100 (at least the sensor element 1) is cooled to the room temperature when forty minutes has passed after the laser welding of the outer tube 4.

This indicates that if the gas sensor 100 is cooled for forty minutes at the room temperature after the laser welding of the outer tube 4, the sensor element 1 is almost certainly cooled to the room temperature, so that the resistance measurement can be performed on the sensor element 1 having the room temperature.

However, in consideration of a measurement error of the heater resistance value $R_H$ or an influence of the sensor element temperature on the measurement accuracy of the gas concentration in the sensor element 1, the gas sensor 100 can be deemed to be sufficiently cooled when the heater resistance value $R_H$ reaches a range of ≤ "the true value" in FIG. 9 +0.005Ω. In case of FIG. 9, this range is certainly satisfied when thirty minutes has passed after the laser welding of the outer tube 4. Accordingly, in the present embodiment, also in view of the productivity, the storage time after the laser welding of the outer tube 4 is set to thirty minutes, and it is checked for each sensor element 1 whether or not the storage time has passed after the laser welding is finished (a step S8). The determination whether or not the storage time has passed is based on the termination time of the laser welding included in the association information.

The gas sensor 100 in which thirty minutes has passed as the storage time (YES in the step S8) goes through a second inspection of the heater resistance value (referred to as a resistance inspection B) (a step S9).

The resistance inspection B is also performed based on the equation (1) in the manner similar to the resistance inspection A. However, differing from the resistance inspection A which can be directly directed to the sensor element 1, that is to say, which enables the probe of the measuring equipment to directly contact the H+ electrode. the H− electrode, and the Ht electrode (the electrode terminals 13f to 13h) of the sensor element 1, in case of the resistance inspection B, both the measurement of the resistance value R1 between the H+ electrode and the Ht electrode and the resistance value R2 between the H− electrode and the Ht electrode are performed via the connector, the lead wire, and the contact point member 21 constituting the contact member 20.

Figure 10:
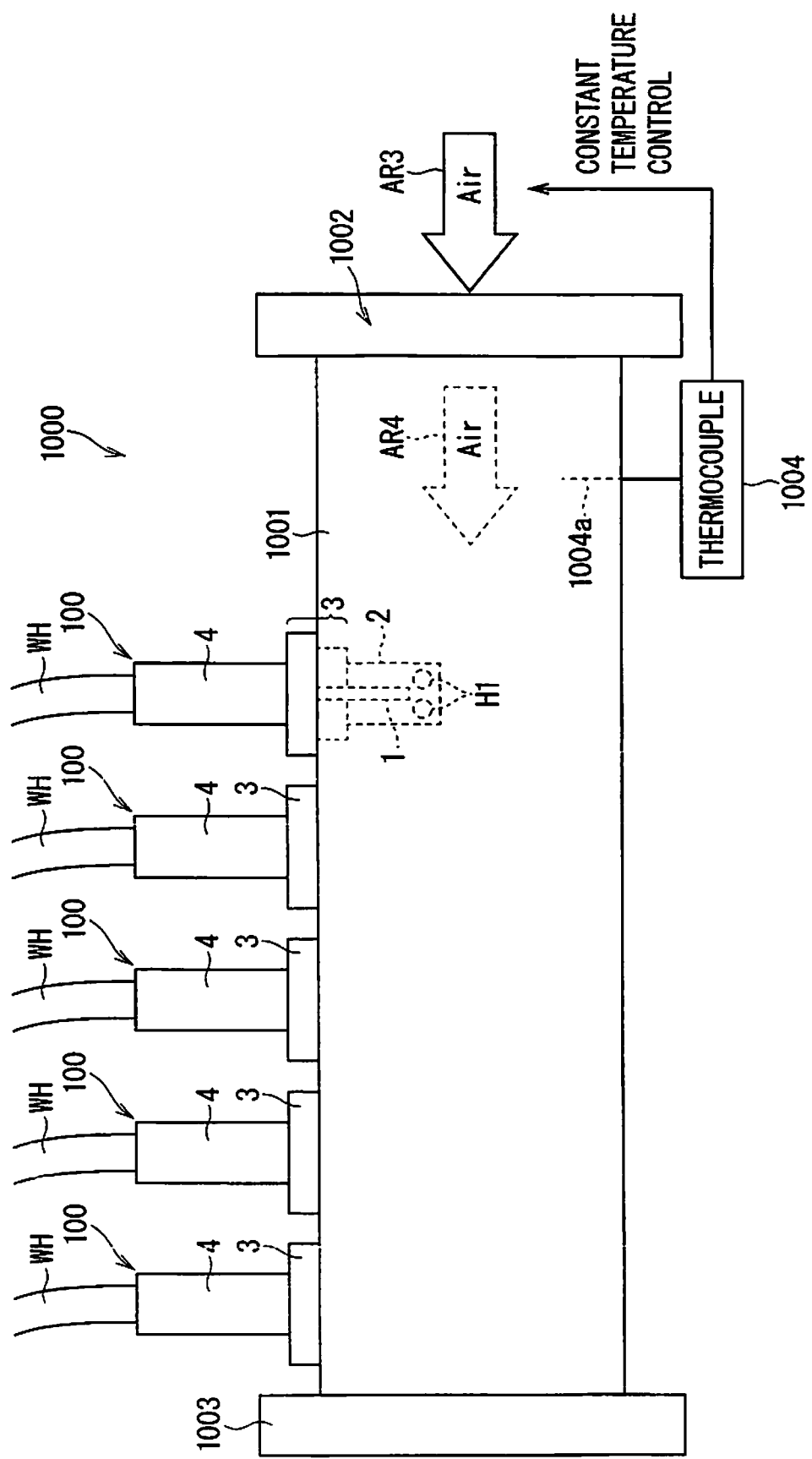
FIG. 10 is a drawing schematically illustrating a configuration of a resistance inspection chamber 1000 used for a resistance inspection B.

FIG. 10 is a drawing schematically illustrating a configuration of the resistance inspection chamber 1000 used for the resistance inspection B in the present embodiment.

The resistance inspection chamber 1000 includes a tubular main body part 1001 where the plurality of gas sensors 100 subjected to the inspection can be arranged in its side surface along its longitudinal direction, a gas inlet 1002 in one end side of the main body part 1001, and an outlet 1003 in other end side of the main body part 1001, so as to introduce air from the gas inlet 1002 as indicated by an arrow AR3 and an arrow AR4. A thermocouple 1004 is inserted near the gas inlet 1002 of the main body part 1001, so that a temperature of the air introduced from the gas inlet 1002 can be kept at constant temperature based on a measurement value measured by the thermocouple 1004.

The gas sensor 100 can be fixed to the side surface of the main body part 1001 with the fixing bolt 3 in a state where a part of the gas sensor 100 covered by the element protection cover 2 is inserted into the body part 1001. In the above fixed state, the sensor element 1 of the gas sensor 100 covered by the element protection cover 2 can contact an atmosphere gas (that is to say, the air) in the body part 1001 flowing into the element protection cover 2 through the through hole H1. Although FIG. 10 shows the five gas sensors 100 fixed to the main body part 1001, the number of the gas sensors 100 fixed to the main body part 1001 is not limited to this exemplification.

The resistance inspection B is performed using the resistance inspection chamber 1000 having the configuration described above, with supplying the air whose temperature is adjusted to 25° C. into the main body part 1001 in a room at a room temperature T of 18° C. to 28° C. That is to say, the resistance value $R_1$ between the H+ electrode and the Ht electrode and the resistance value $R_2$ between the H− electrode and the Ht electrode are measured in the air in the manner similar to the resistance inspection A, and the heater resistance value $R_H$ is calculated from those values by the equation (1).

Then, the heater resistance value $R_H$ obtained by the above calculation is corrected to a value in the case of 25° C. based on the following equation including the room temperature T (° C.) in measurement, and the value is defined as a heater resistance value $R_{HB}$ obtained in the resistance inspection B.

$$R_{HB}=R_H(1+25\alpha+25^2\beta)/(1+\alpha T+\beta T^2) \qquad (2)$$

α and β are values defined by a material of the heater 70, and in a case of platinum, for example, α=3930 and β=−0.6.

The rejected gas sensor 100 whose heater resistance value $R_{HB}$ calculated based on the equation (2) does not meet the predetermined standard (for example, the predetermined resistance value range) (NG in the step S9) is excluded from a manufacturing object (an inspection object) thereafter. When the standard of the heater resistance value $R_{HB}$ includes the resistance value range, the resistance value range is set as a range of the resistance value allowed in the actual use of the gas sensor 100.

With regard to the accepted gas sensor 100 whose heater resistance value $R_{HB}$ calculated based on the equation (2) meets the predetermined standard (OK in the step S9), the element identification information of the sensor element 1 incorporated into the gas sensor 100 and the heater resistance value $R_{HB}$ are associated with each other (a step S10). This association can be performed in the manner similar to the association of the termination time of the laser welding described above. That is, the associated information may be recorded as an electronic data, may be recorded in or outputted to a paper medium, or may be laser-marked on the outer tube 4.

After the association is finished, the associated information is subsequently read out, and the heater resistance value $R_{HA}$ obtained in the resistance inspection A and the heater resistance value $R_{HB}$ obtained in the resistance inspection B are compared (a step S11).

When a difference value between the heater resistance value $R_{HA}$ and the heater resistance value $R_{HB}$ exceeds a predetermined threshold value as a result of the comparison (NG in the step S11), the gas sensor 100 is excluded from a manufacturing object (an inspection object) thereafter.

In the meanwhile, the difference between the heater resistance value $R_{HA}$ and the heater resistance value $R_{HB}$ falls within the predetermined threshold value (OK in the step S11), the gas sensor 100 goes through other characteristic inspection process (a step S12). The gas sensor 100 in which a defect is found in the characteristic inspection (NG in the step S12) is excluded from a shipping object. In the meanwhile, the gas sensor 100 in which the defect is not found in the characteristic inspection (OK in the step S12) is shipped as a product at an appropriate timing (a step S13).

<Determination of Presence or Absence of Assembly Defect Based on Comparison of Heater Resistance Value>

The step S11 in the procedure shown in FIG. 8 allows the difference within the range of the predetermined threshold value between the heater resistance value $R_{HA}$ and the heater resistance value $R_{HB}$. It is because of consideration that the measurement method and the measurement range of those heater resistance values are actually different from each other, so that a slight difference may occur between the value of the heater resistance value $R_{HA}$ obtained by the measurement in which the electrode terminals 13*f* to 13*h* of the sensor element 1 are directly used, and the value of the heater resistance value $R_{HB}$ obtained by the measurement via the connector, the lead wire, and the contact point member 21, even when those measurements are accurately performed and the resistance values of the connector, the lead wire, and the contact point member 21 are sufficiently small, and moreover, because of that some temperature variation is permitted when the concentration measurement is actually performed using the gas sensor 100.

However, the gas sensor 100 normally assembled is considered to have a low possibility that the large difference occurs between the heater resistance value $R_{HA}$ and the heater resistance value $R_{HB}$. Accordingly, when the difference which exceeds the threshold value occurs in the difference value between the heater resistance value $R_{HA}$ and the heater resistance value $R_{HB}$, it can be determined that some defect has occurred in assembling the gas sensor 100, and the gas sensor 100 in which the difference has occurred can be determined to be an assembly reject product and excluded from the manufacturing object.

Figure 11:
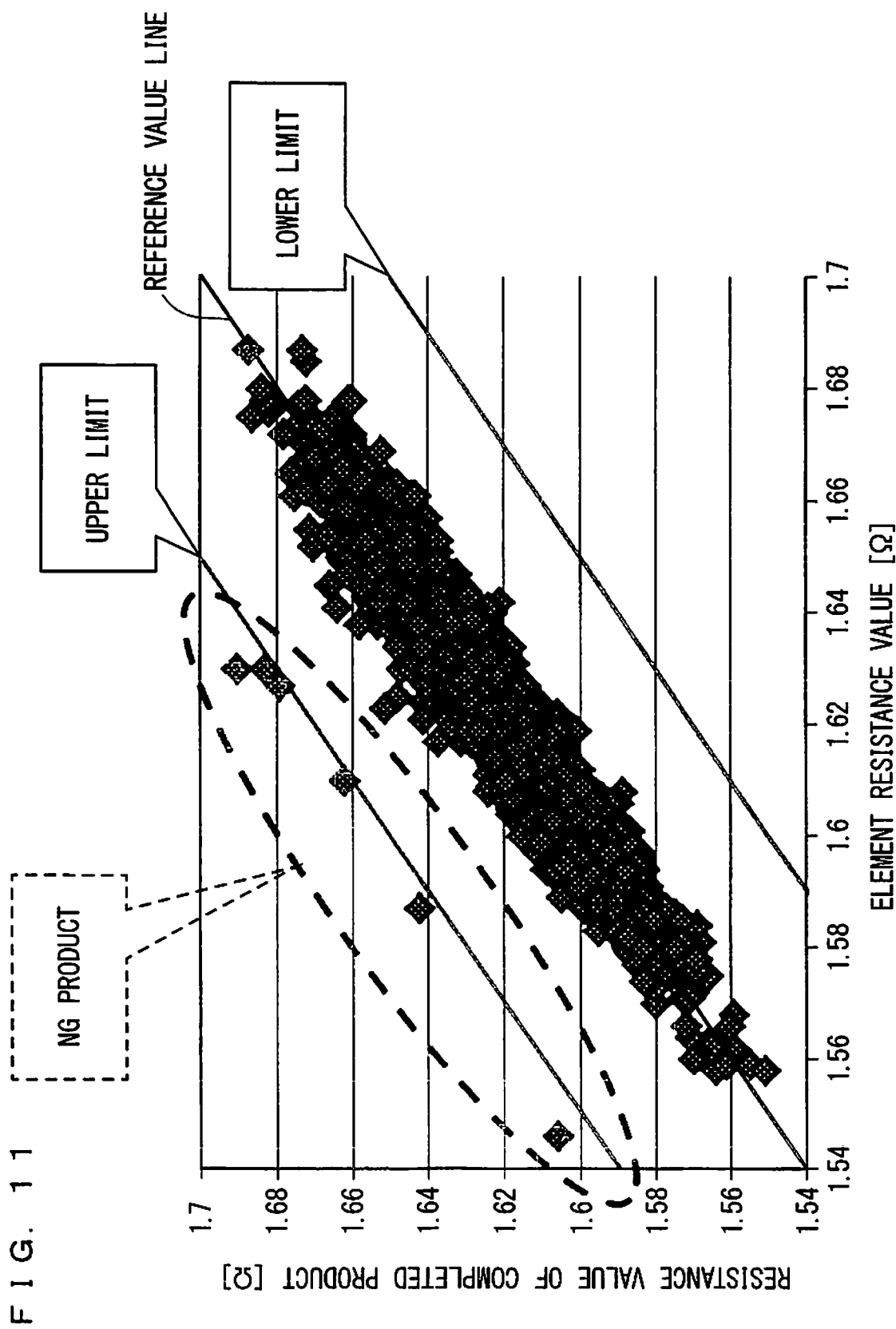
FIG. 11 is a drawing plotting, with respect to a large number of gas sensors 100, a value of a heater resistance value $R_{HB}$ for a value of a heater resistance value $R_{HA}$.

FIG. 11 is a drawing plotting, with respect to a large number of gas sensors 100, the value of the heater resistance value $R_{HB}$ (shown as "resistance value of completed product" in FIG. 11) for the value of the heater resistance value $R_{HA}$ (shown as "element resistance value" in FIG. 11). All of the gas sensors 100 which are subject to the plotting have passed the resistance inspection A which has a standard that the heater resistance value $R_{HA}$ satisfies 1.43Ω to 1.87Ω and the resistance inspection B which has a standard that the heater resistance value $R_{HB}$ satisfies 1.41Ω to 1.89Ω.

Furthermore, in FIG. 11, a line which satisfies the heater resistance value $R_{HB}$=the heater resistance value $R_{HA}$ is drawn as a reference line, and, under the definition that defines ±0.05Ω is a threshold value for the difference value between the heater resistance value $R_{HA}$ and the heater resistance value $R_{HB}$, an upper limit line of the difference value which satisfies the heater resistance value $R_{HB}$=the heater resistance value $R_{HA}$+0.05Ω and a lower limit line of the difference value which satisfies the heater resistance value $R_{HB}$=the heater resistance value $R_{HA}$−0.05Ω are additionally drawn. The error of the heater resistance value of ±0.05Ω corresponds to an error of a heater heating temperature of approximately ±10° C.

In FIG. 11, a large majority of data points are distributed around the reference line between the upper limit line and the lower limit line, however, only five data points are located above the upper limit line. That is to say, the gas sensors 100 providing these five points have a large change between the heater resistance value $R_{HB}$ and the heater resistance value $R_{HA}$ compared with the other gas sensor 100. This suggests that these five gas sensors 100 pass the resistance inspection B, however, they have a state which differs from that of the other gas sensor 100 therein.

Then, taking the gas sensors 100 providing these data points, it was recognized that talc particles (ceramic powder) constituting the powder compact 9 was sandwiched between the electrode terminal 13 of the sensor element 1 and the contact point member 21 of the contact member 20. The result indicates that, in the gas sensor 100 whose difference value between the heater resistance value $R_{HA}$ and the heater resistance value $R_{HB}$ exceeds the threshold value, a defect actually occurs in a contact area between the electrode terminal 13 and the contact point member 21 with a high probability. Accordingly, the comparison of the heater resistance value performed in the step S11 of the procedure shown in FIG. 8 is deemed to be effective in detecting an assembly defect which cannot always be detected only by performing the resistance inspection A or B.

In the present embodiment, as described above, an element identification number which enables a unique identification of the individual sensor element 1 is provided to all of the sensor element 1, and the measurement value in the resistance inspections A and B for the individual sensor element 1 (the heater resistance value $R_{HA}$ and the heater resistance value $R_{HB}$) is associated with the element identification number for the sensor element 1, so that an evaluation of the difference value of the heater resistance value can also be separately performed on the individual sensor element 1. Accordingly, in the present embodiment, the presence or absence of the assembly defect in the individual gas sensor 100 can be reliably determined also in case of the mass-production of the gas sensor 100. In other words, traceability in the individual sensor element 1 is ensured.

Moreover, since the heater resistance value $R_{HA}$ and the heater resistance value $R_{HB}$ are associated with the element identification information, the association information is taken over to the next process together with the sensor element or a product in middle of assembly even when the process included in the procedure shown in FIG. 8 is performed at a different place, so that the inspection can be reliably performed on the individual sensor element.

As described above, according to the present embodiment, in the case that the gas sensor into which the sensor element is incorporated inside is mass-produced, the inspection of the resistance value of the heater included in the individual sensor element is performed in the two stages, that is to say, the first inspection performed on the sensor element before incorporated and the second inspection performed after the gas sensor is completed. The difference value of the heater resistance value obtained by these two resistance inspection is then compared with the predetermined threshold value, and when the difference value exceeds the threshold value, it is determined that the assembly defect (more specifically, the defect in the contact state between the electrode terminal of the sensor element and the contact point member of the contact member) occurs in the gas sensor. Accordingly, the sensor element which has the abnormal heater resistance value can be excluded before assembling the gas sensor, and the gas sensor which the sensor element having the normal heater resistance value is incorporated into but has the assembly defect can also be excluded from the shipping object.

MODIFICATION EXAMPLE

Applicable is an embodiment that an element identification information is defined with respect only to the sensor element 1 which has passed the resistance inspection A, and based on the element identification information, an element identification mark ID is provided to the sensor element 1. In this case, also applicable is an embodiment that the resistance value obtained in the resistance inspection A and the other information are collectively bar-coded or two-dimensionally-coded in addition to the element identification information.

If the arrangement position of the individual sensor element 1 and gas sensor 100 is fixedly determined in the manufacturing process of the gas sensor 100 and the association between the arrangement position and the individual sensor element 1 and gas sensor 100 is reliably performed, the individual sensor element 1 and gas sensor 100 may be identified using the arrangement position. In this case, the position information of the individual sensor element 1 and gas sensor 100 substitutes the element identification information, so that the element identification mark ID needs not be provided to the sensor element 1.

The invention claimed is:

1. A method of inspecting a presence or absence of an assembly defect of a gas sensor into which a sensor element is incorporated inside, said gas sensor comprising:
   a first gas sensor constituting member having an insertion opening into which said sensor element is inserted; and
   a second gas sensor constituting member including said sensor element which partially protrudes from said second gas sensor constituting member, wherein:
   in said gas sensor, a part of said sensor element which protrudes from said second gas sensor constituting member is inserted into said insertion opening, so that said first gas sensor constituting member and said second gas sensor constituting member are integrated with each other,
   said sensor element includes a heater made up of a resistance heating member therein and also includes an electrode terminal for the heater in a surface the sensor element, and
   said first gas sensor constituting member includes a contact point member which contacts said electrode terminal in a state where said sensor element is inserted into said insertion opening, and
   said method comprising steps of:
   determining an identification information enabling a unique identification of said sensor element;
   measuring a resistance value of said heater of said sensor element at a first time to obtain a first resistance value, said first time being a time before said sensor element is incorporated into said second gas sensor constituting member, and associating said first resistance value with said identification information for said sensor element;
   measuring said resistance value of said heater at a second time via at least said contact point member to obtain a second resistance value, said second time being a time after said sensor element is incorporated into said second gas sensor constituting member and after said first gas sensor constituting member and said second gas sensor constituting member have been integrated with each other, and associating said second resistance value with said identification information for said sensor element; and
   comparing a difference value between said first resistance value and said second resistance value associated with an identical identification information with a predetermined threshold value, and when said difference value exceeds said predetermined threshold value, determining that an assembly defect occurs in said gas sensor into which said sensor element, to which said identical identification information is provided, is incorporated.

2. The method of inspecting said gas sensor according to claim 1, wherein
   said second gas sensor constituting member is formed with a plurality of annularly-mounted members including a ceramic powder compact annularly mounted to said sensor element.

3. The method of inspecting said gas sensor according to claim 2, wherein
   in said gas sensor, an outer tube covering said first gas sensor constituting member is laser-welded to said second gas sensor constituting member being integrated with said first gas sensor constituting member,
   performing a measurement of said resistance value of said heater for obtaining said first resistance value in air at room temperature, and performing a measurement of said resistance value of said heater for obtaining said second resistance value in air when thirty minutes has passed after completing said laser welding of said outer tube.

4. The method of inspecting said gas sensor according to claim 3, wherein
in a step of determining said identification information, an identification mark including said identification information is provided to said sensor element, and
said identification information obtained by reading said identification mark with a predetermined reading means is associated with said first and second resistance values.

5. The method of inspecting said gas sensor according to claim 2, wherein
in a step of determining said identification information, an identification mark including said identification information is provided to said sensor element, and
said identification information obtained by reading said identification mark with a predetermined reading means is associated with said first and second resistance values.

6. The method of inspecting said gas sensor according to claim 1, wherein
in said gas sensor, an outer tube covering said first gas sensor constituting member is laser-welded to said second gas sensor constituting member being integrated with said first gas sensor constituting member,
performing a measurement of said resistance value of said heater for obtaining said first resistance value in air at room temperature, and
performing a measurement of said resistance value of said heater for obtaining said second resistance value in air when thirty minutes has passed after completing said laser welding of said outer tube.

7. The method of inspecting said gas sensor according to claim 6, wherein
in a step of determining said identification information, an identification mark including said identification information is provided to said sensor element, and
said identification information obtained by reading said identification mark with a predetermined reading means is associated with said first and second resistance values.

8. The method of inspecting said gas sensor according to claim 1, wherein
in a step of determining said identification information, an identification mark including said identification information is provided to said sensor element, and
said identification information obtained by reading said identification mark with a predetermined reading means is associated with said first and second resistance values.

9. A method of manufacturing a gas sensor, comprising steps of:
preparing a sensor element including a heater made up of a resistance heating member therein and an electrode terminal for the heater in a surface of the sensor element;
determining an identification information enabling a unique identification of said sensor element;
measuring a resistance value of said heater at a first time to obtain a first resistance value and associating said first resistance value with said identification information for said sensor element;
assembling a first gas sensor constituting member having an insertion opening into which said sensor element is inserted and a contact point member contacting said electrode terminal in a state where said sensor element is inserted into said insertion opening;
after measuring said resistance value of said heater at said first time, assembling a second gas sensor constituting member so that said sensor element partially protrudes;
inserting a part of said sensor element which protrudes from said second gas sensor constituting member into said insertion opening of said first gas sensor constituting member to integrate said first gas sensor constituting member and said second gas sensor constituting member;
measuring said resistance value of said heater at a second time via at least said contact point member to obtain a second resistance value, said second time being a time after said sensor element is incorporated into said second gas sensor constituting member and alter said first gas sensor constituting member and said second gas sensor constituting member have been integrated with each other and associating said second resistance value with said identification information for said sensor element; and
comparing a difference value between said first resistance value and said second resistance value associated with an identical identification information, and when said difference value exceeds said predetermined threshold value, determining that an assembly defect occurs in said gas sensor into which said sensor element, to which said identical identification information is provided, is incorporated.

10. The method of manufacturing said gas sensor according to claim 9, wherein
said step of assembling said second gas sensor constituting member includes a step of annularly mounting a plurality of annularly-mounted members including a ceramic powder compact to said sensor element.

11. The method of manufacturing said gas sensor according to claim 10, further comprising steps of:
after integrating said first gas sensor constituting member and said second gas sensor constituting member, laser-welding an outer tube covering said first gas sensor constituting member to said second gas sensor constituting member, wherein
a measurement of said resistance value of said heater for obtaining said first resistance value is performed in air at room temperature, and
a measurement of said resistance value of said heater for obtaining said second resistance value is performed in air when thirty minutes has passed after completing said laser welding of said outer tube.

12. The method of manufacturing said gas sensor according to claim 11, wherein
in a step of determining said identification information, an identification mark including said identification information is provided to said sensor element, and
said identification information obtained by reading said identification mark with a predetermined reading means is associated with said first and second resistance values.

13. The method of manufacturing said gas sensor according to claim 10, wherein
in a step of determining said identification information, an identification mark including said identification information is provided to said sensor element, and said identification information obtained by reading said identification mark with a predetermined reading means is associated with said first and second resistance values.

14. The method of manufacturing said gas sensor according to claim 9, further comprising steps of:

after integrating said first gas sensor constituting member and said second gas sensor constituting member, laser-welding an outer tube covering said first gas sensor constituting member to said second gas sensor constituting member, wherein a measurement of said resistance value of said heater for obtaining said first resistance value is performed in air at room temperature, and a measurement of said resistance value of said heater for obtaining said second resistance value is performed in air when thirty minutes has passed after completing said laser welding of said outer tube.

15. The method of manufacturing said gas sensor according to claim 14, wherein in a step of determining said identification information, an identification mark including said identification information is provided to said sensor element, and said identification information obtained by reading said identification mark with a predetermined reading means is associated with said first and second resistance values.

16. The method of manufacturing said gas sensor according to claim 9, wherein in a step of determining said identification information, an identification mark including said identification information is provided to said sensor element, and said identification information obtained by reading said identification mark with a predetermined reading means is associated with said first and second resistance values.

17. A method of inspecting a presence or absence of an assembly defect of a gas sensor into which a sensor element is incorporated inside, said gas sensor comprising:

a first gas sensor constituting member having an insertion opening into which said sensor element is inserted; and a second gas sensor constituting member including said sensor element which partially protrudes from said second gas sensor constituting member, wherein:

in said gas sensor, a part of said sensor element which protrudes from said second gas sensor constituting member is inserted into said insertion opening, so that said first gas sensor constituting member and said second gas sensor constituting member are integrated with each other, said sensor element includes a heater made up of a resistance heating member therein and also includes an electrode terminal for the heater in a surface of the sensor element, and said first gas sensor constituting member includes a contact point member which contacts said electrode terminal in a state where said sensor element is inserted into said insertion opening, and said method comprising steps of:

measuring a resistance value of said heater of said sensor element at a first time to obtain a first resistance value, said first time being a time before said sensor element is incorporated into said second gas sensor constituting member;

measuring said resistance value of said heater at a second time via at least said contact point member to obtain a second resistance value, said second time being a time after said sensor element is incorporated into said second as sensor constituting member and after said first gas sensor constituting member and said second gas sensor constituting member have been integrated with each other; and comparing a difference value between said first resistance value and said second resistance value with a predetermined threshold value, and when said difference value exceeds said predetermined threshold value, determining that an assembly defect occurs in said gas sensor.

* * * * *